United States Patent
Perryman et al.

(10) Patent No.: US 11,826,082 B1
(45) Date of Patent: Nov. 28, 2023

(54) LAMINOPLASTY HINGED PLATE WITH INTEGRATED SPACER

(71) Applicant: Choice Spine, LLC, Knoxville, TN (US)

(72) Inventors: John Abe Perryman, Columbia, TN (US); Larry T. Khoo, Studio City, CA (US)

(73) Assignee: Choice Spine, LLC, Knoxville, TN (US)

( * ) Notice: Subject to any disclaimer, the term of this patent is extended or adjusted under 35 U.S.C. 154(b) by 831 days.

(21) Appl. No.: 16/448,514

(22) Filed: Jun. 21, 2019

Related U.S. Application Data

(60) Provisional application No. 62/691,904, filed on Jun. 29, 2018.

(51) Int. Cl.
*A61B 17/70* (2006.01)
*A61L 31/02* (2006.01)

(52) U.S. Cl.
CPC ...... *A61B 17/7071* (2013.01); *A61B 17/7059* (2013.01); *A61L 31/022* (2013.01)

(58) Field of Classification Search
CPC .................................................. A61B 17/7071
See application file for complete search history.

(56) References Cited

U.S. PATENT DOCUMENTS

| | | | |
|---|---|---|---|
| 6,635,087 B2 | 10/2003 | Angelucci et al. | |
| 7,264,620 B2 | 9/2007 | Taylor | |
| 8,105,366 B2 | 1/2012 | Null et al. | |
| 8,133,280 B2 | 3/2012 | Voellmicke et al. | |
| 8,172,875 B2 | 5/2012 | Taylor | |
| 8,246,660 B2 | 8/2012 | Boris et al. | |
| 8,926,664 B1 * | 1/2015 | Millhouse | A61B 17/7059 606/246 |
| 2002/0120335 A1 | 8/2002 | Angelucci et al. | |
| 2011/0046680 A1 * | 2/2011 | Khanna | A61B 17/7071 606/279 |
| 2013/0060283 A1 | 3/2013 | Suh et al. | |

* cited by examiner

*Primary Examiner* — Andrew Yang
(74) *Attorney, Agent, or Firm* — Luedeka Neely, P.C.

(57) ABSTRACT

A single device desirably configured for use at complete cut location of an open door laminoplasty surgical site, and to be adjustable in size and orientation so that they may be adapted to the site at the time of surgery. The device is a one-piece construct of a base with an integrated spacer, with an extension hingedly connected to the base. The base and spacer are integrally formed of material that is not bone or bone-like, such as titanium. The spacer is devoid of void or open areas and includes arched proximal ends.

6 Claims, 3 Drawing Sheets

LAMINOPLASTY HINGED PLATE WITH INTEGRATED SPACER

CROSS-REFERENCE TO RELATED APPLICATION

This application claims priority to U.S. Provisional Application No. 62/691,904 filed Jun. 29, 2018, entitled LAMINOPLASTY HINGED PLATE WITH INTEGRATED SPACER, incorporated herein by reference in its entirety.

FIELD

This disclosure relates to the field of laminoplasty surgery. More particularly, this disclosure relates to hinged plate structures with an integrated spacer and the use thereof in laminoplasty surgery.

BACKGROUND

Laminoplasty is a spinal surgery procedure in which the lamina at the posterior of the spine is removed. Improvement is desired in devices utilized during laminoplasty procedures. In an open door laminoplasty, a type of laminoplasty procedure, two cuts are made to relieve spinal pressure. A cut referred to as the thru cut is made completely through one side of a vertebrae between a lamina and a lateral mass of the vertebrae. A partial cut referred to as a Greenstick fracture is made on the opposite lateral side. This results in the lamina being hinged about the partial cut. Implant devices, such as hinged plates, can be affixed to the spine at the locations of the two cuts to provide support.

A separate spacer is often utilized with the implant to maintain the original or a desired spacing of the lamina and the lateral mass of the vertebrae. Conventionally, the spacer is made of a material configured to promote bone growth onto the spacer. For example, conventional spacers are typically made of a natural or synthetic allograft or like material. That is, bone or bone-like material. These spacers made of bone or bone-like materials often degrade when a bone screw or like fastener is threaded or attached to the spacer during attachment of the implant to the spacer.

Alternatively, if a non-bone like material is used to provide a spacer, the spacer is conventionally configured to include void areas, and often bone or bone-like material is deposited into the void areas. Spacers of this construction are overly complicated to produce and desire improvement as well.

Moreover, it has been observed that various problems and shortcomings are associated with the conventional practice of having to connect a spacer to an implant.

What is desired is an integrated implant and spacer that overcomes the various shortcomings of the prior art.

SUMMARY

The present disclosure relates to an integrated implant and spacer configuration configured for use at the complete or thru cut location of an open door laminoplasty.

In one aspect, an implant according to the disclosure includes a spacer integrated with a base and an extension hingedly connected to the base.

In another aspect, the disclosure provides an implant assembly for use at a thru cut location of an open door laminoplasty surgical procedure. The assembly includes a spacer provided by a solid spacer body being devoid of void or open areas for holding bone or bone like material or for promoting bone growth; and an extension hingedly connected to the base.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
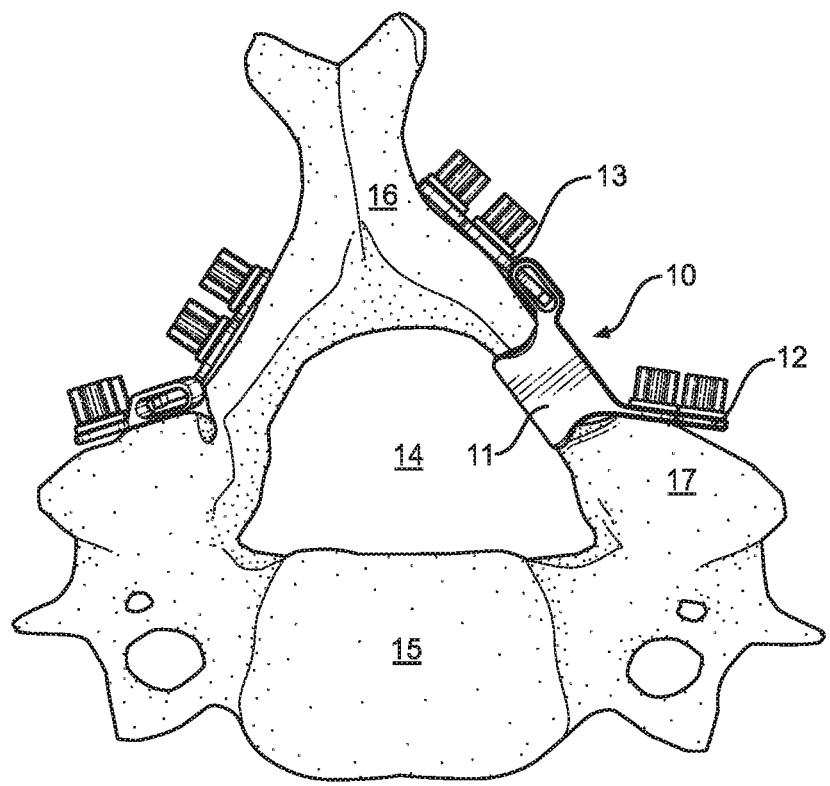
FIGS. 1-3 show a spine section on which an open door laminoplasty has been performed, with implants, such as hinged plates installed on both the thru cut and the Greenstick fracture. An integrated implant according to the disclosure having a hinged implant and spacer co-formed therewith is shown installed on the thru cut, with the spacer portion located to maintain the spacing of the lamina and the lateral mass of the vertebrae.
Figure 2:
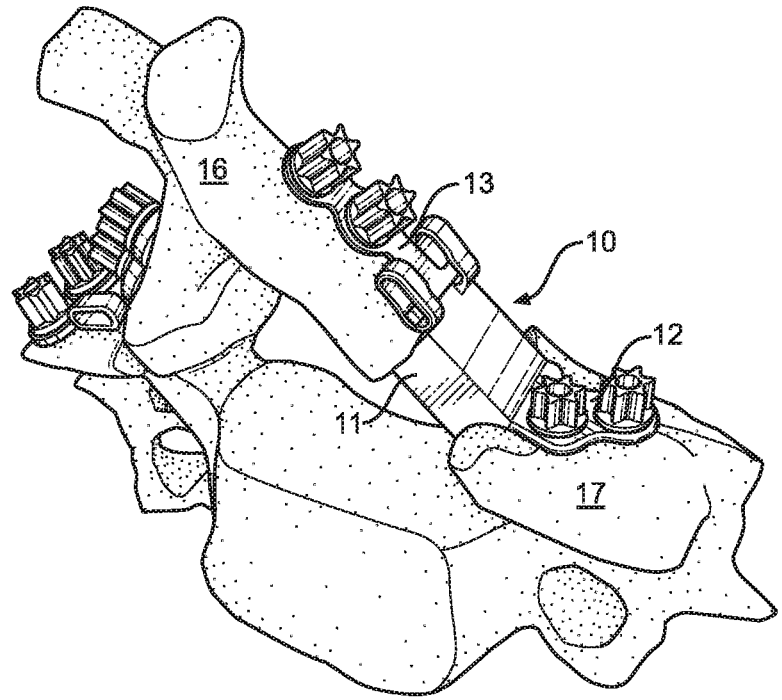
Figure 3:
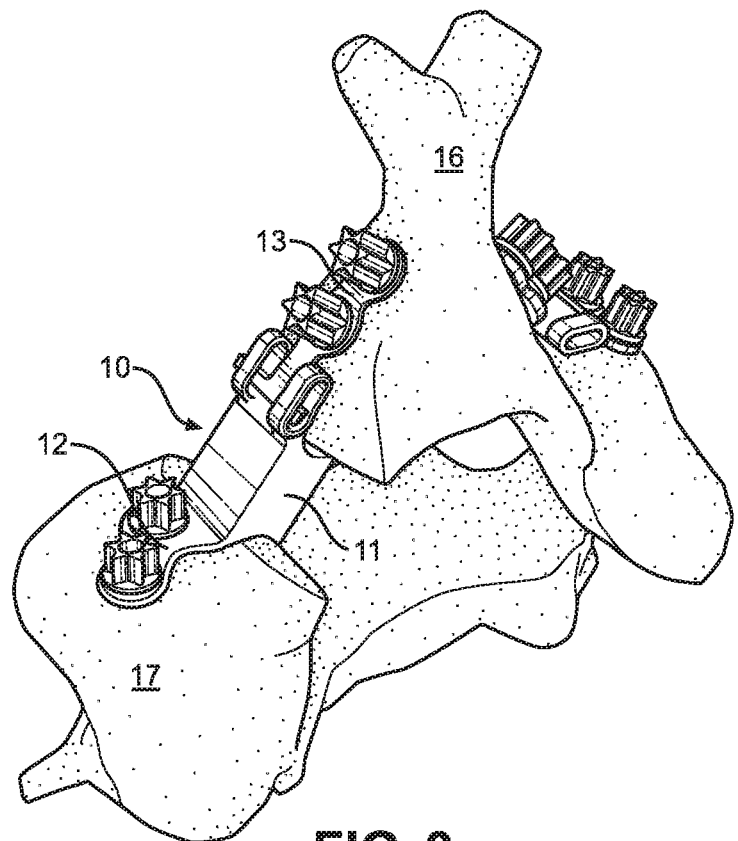

With initial reference to FIGS. 1-3, there is shown an integrated implant device 10 used in an open door laminoplasty surgical procedure. The device 10 includes a one-piece structure defining a spacer 11 integrated with an elongate base 12 configured as a plate. An extension 13 is hingedly connected to the base 12.

The device 10 is desirable configured to be adjustable in size and orientation so that they may be adapted to the site at the time of the laminoplasty surgery. All of the components of the device 10 are desirably made of titanium. The spacer 11 portion of the device 10 is preferably heavy grit blasted resulting in a smooth texture to provide firmer grip.

A hinged plate is an implant of the type having a plate portion with an extension hingedly attached. If a spacer is used, the spacer is typically secured to an underside of the plate portion. The present disclosure overcomes many of the shortcomings associated with the use of a hinged plate implant and separate spacer.

In the case of the integrated device of the disclosure, there is not a plate portion per se. Rather, an upper surface of the spacer provides the material of the implant normally supplied by the plate. The present structure is stronger than the combination of a plate and spacer and avoids many of the shortcomings associated with providing a separate plate and spacer.

Returning to FIGS. 1-3, in an open door laminoplasty, a complete cut 14 known as a thru cut has been made through one side of a vertebrae 15 between a lamina 16 and a lateral mass 17 of the vertebrae 15. The integrated device 10 is particularly suitable for use with such a surgical procedure and as shown, is placed at the complete cut 14 to fill the lamina 16 and lateral mass 17 of the vertebrae 15 gap. As shown, the shape of the spacer 11 advantageously is formed to correspond to contours to the anatomy of the lamina 16 for a secured fit.

The spacer 11 is solid and devoid of open or void areas for holding bone or bone like material, and devoid of void areas of the type conventionally provided in an attempt to promote bone growth to conventional spacers. However, the configuration of the spacer 11 has been observed to enable a snug fit and accomplish desired growth of bone without such open or void areas conventionally utilized. This results in a structure that is uncomplicated to produce as compared to conventional spacer and implant constructions.

The device 10 is also advantageously configured to be able to adjust in length and angular orientation. The ability of the hinges to adjust in length enables a reduction in the inventory of hinge sizes and enables a hinge to be adjusted in size. The ability to adjust the angular orientation of the hinge enables the hinge to be oriented to lie flush with on the lamina 16 without having to bend the material of the hinge as is done conventionally.

Figure 4:
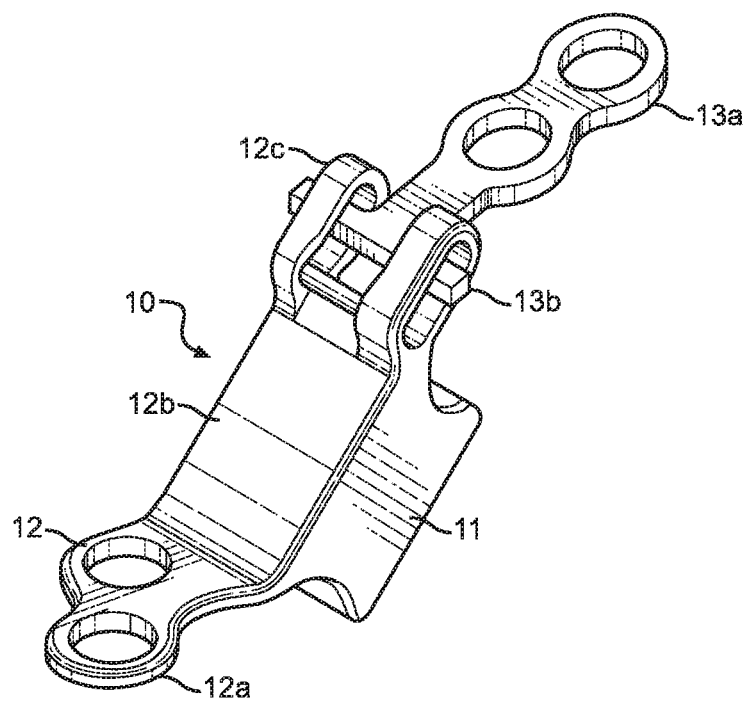
FIGS. 4-6 are detailed views of an integrated implant according to the disclosure having a spacer integrated with an implant.
Figure 5:
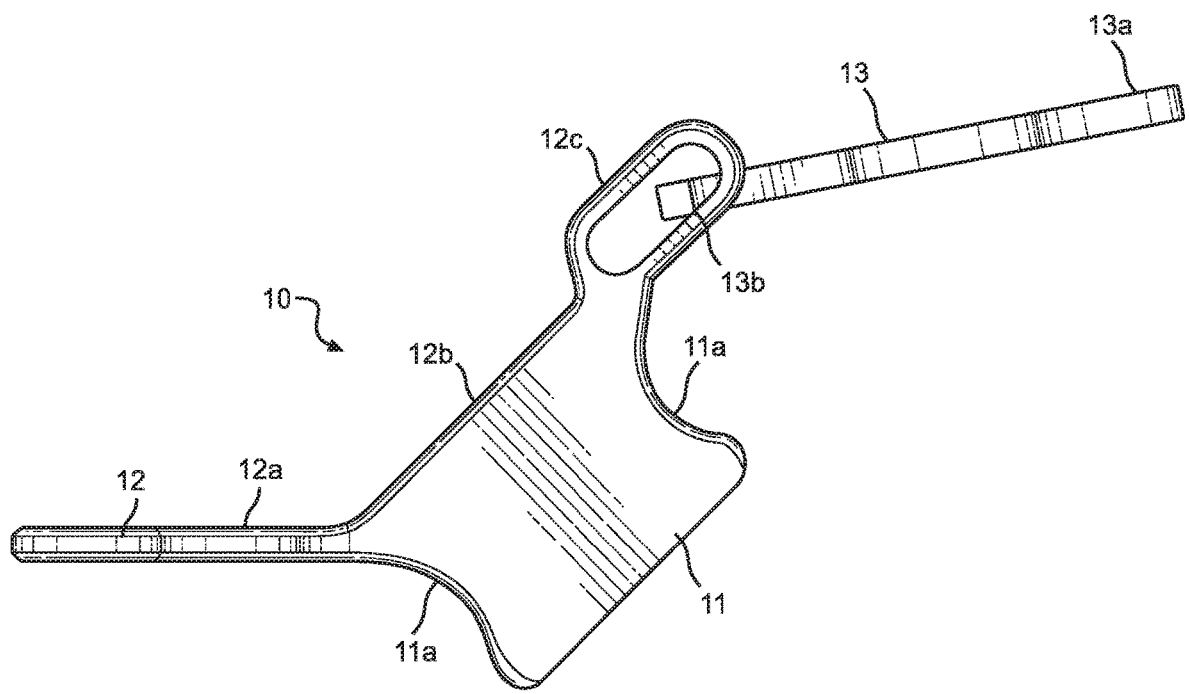
Figure 6:
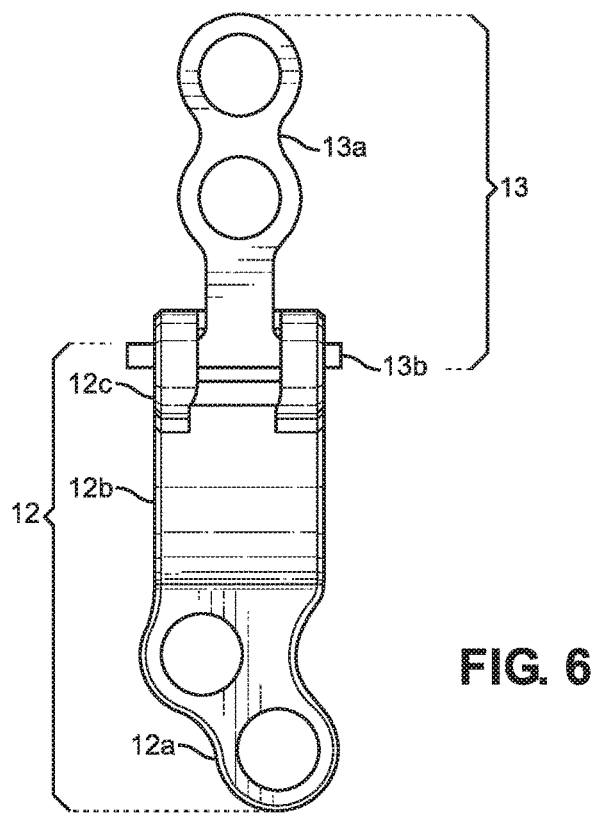

As depicted in FIGS. 4-6, the extension 13 is adjustably connected to the base 12 in a manner that enables adjustment of both the length and the angular orientation of the device 10. As depicted, apertures are provided on the base 12 and the extension for passage of fasteners to fasten the base 12 and the extension 13 to the lamina 16 and the lateral mass 17.

The integrated spacer 11 is shown in FIG. 5 connected to the back 12b of the base 12. The integrated spacer 11 has two arched proximal ends 11a that are arched away from the spinal cord and configured as concave arches extending into the body of the spacer 11. These features enable the spacer to be arched away from the spine to better fit the spine.

The base 12 includes a seat 12a and a back 12b extending from the seat 12a in a reclined relationship, preferably at an angle of from about 30 to about 75 degrees, most preferably about 45 degrees. The back 12b is connected to the integrated spacer 11 to fill the space between the lamina 16 and the lateral mass 17 of the vertebrae 15. A pair of spaced apart and aligned offset ovals or slots 12c are positioned at the distal or free end of the back 12b.

The extension 13 is T-shaped and includes an elongated body 13a having a head 13b at an end of the body 13a. The head 13b is slightly longer on one side than the other. The device 10 is assembled by placing the head 13b of the extension 13 to span between the offset slots 12c of the back 12b of the base 12. Once attached, the head 13b may freely pivot within the slots 12c to permit various relative angular orientations.

The device 10 is shown installed at the site of the complete cut 14 known as the thru cut and fixed in place with fasteners in FIGS. 1-3. As seen, the device 10 is able to adjust in length and angular orientation to correspond to the structure of the lamina 16 to be spanned at the site of the complete cut 14.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated. All such modifications and variations are within the scope of the disclosure

The invention claimed is:

1. A surgical implant, comprising: a one-piece structure defining a spacer integrated with an elongate base extending from the spacer and configured as a plate; and an extension hingedly connected to the spacer opposite the base; wherein the spacer includes a top face and arched proximal ends at opposite ends of the top face, the ends being configured as concave arches extending into the spacer.

2. The implant of claim 1, wherein the implant is configured for use at the complete or thru cut location of an open door laminoplasty.

3. The implant of claim 1, wherein the spacer is a solid body that is devoid of void or open areas for holding bone or bone like material or for promoting bone growth.

4. The implant of claim 1, wherein the implant is made of titanium.

5. An implant assembly for use at a thru cut location of an open door laminoplasty surgical procedure, the assembly comprising a one-piece structure defining a spacer provided by a solid spacer body being devoid of void or open areas for holding bone or bone like material for promoting bone growth and an elongate base configured as a plate; and an extension hingedly connected to the spacer opposite the base; wherein the spacer includes a top face and arched proximal ends at opposite ends of the top face, the ends being configured as concave arches extending into the spacer.

6. The assembly of claim 5, wherein the spacer is made of titanium.

* * * * *